(12) United States Patent
Nakayama et al.

(10) Patent No.: US 6,962,780 B2
(45) Date of Patent: Nov. 8, 2005

(54) METHOD FOR SYNTHESIS OF NUCLEIC ACIDS

(75) Inventors: Tomoko Nakayama, Tsukuba (JP); Naoyuki Nishimura, Tsukuba (JP)

(73) Assignee: Shimadzu Corporation, Kyoto (JP)

( * ) Notice: Subject to any disclaimer, the term of this patent is extended or adjusted under 35 U.S.C. 154(b) by 100 days.

(21) Appl. No.: 09/843,819

(22) Filed: Apr. 30, 2001

(65) Prior Publication Data

US 2002/0102660 A1 Aug. 1, 2002

(30) Foreign Application Priority Data

Jun. 12, 2000 (JP) ........................................ 2000-174991

(51) Int. Cl.$^7$ .......................... C12Q 1/68; C12P 19/34; C07H 21/02; C07H 21/04
(52) U.S. Cl. ........................ 435/6; 435/91.2; 536/23.5; 536/24.31; 536/24.33
(58) Field of Search .......................... 435/6, 91.1, 91.2; 536/23.1, 24.1, 24.31

(56) References Cited

U.S. PATENT DOCUMENTS

| | | | | |
|---|---|---|---|---|
| 4,368,314 A | * | 1/1983 | Endo et al. ................... | 528/89 |
| 4,683,280 A | * | 7/1987 | Ukachi et al. ................. | 528/71 |
| 4,820,309 A | * | 4/1989 | Holliger ........................ | 8/437 |
| 4,948,724 A | * | 8/1990 | Yin .............................. | 435/13 |
| 4,978,757 A | * | 12/1990 | Kelly et al. ................... | 548/421 |
| 5,369,096 A | * | 11/1994 | Yamada et al. ............... | 514/61 |
| 5,432,065 A | * | 7/1995 | Fuller .......................... | 435/91.1 |
| 5,707,802 A | * | 1/1998 | Sandhu et al. ................. | 435/6 |
| 5,972,618 A | * | 10/1999 | Bloch ............................ | 435/6 |
| 6,054,501 A | * | 4/2000 | Taniguchi et al. ............ | 522/31 |
| 6,183,998 B1 | * | 2/2001 | Ivanov et al. .............. | 435/91.2 |

OTHER PUBLICATIONS

Mercier et al.(Nucleic Acids Research, vol. 18, No. 19) 1990 p. 5908.*
Accession No. BC025925 with alignments to Seq. ID No. 8 and 9 of US 6,183,998.*
Barnes, Wayne. "PCR amplification of up to 35–kb . . . ", Mar. 1994, Genetics vol. 91 pp. 2216–2220.*
Henke, Wolfgang. "Betaine improves the PCR amplification of GC–rich . . . ", Nucleic Acids Research, Aug. 1997, vol. 25, pp. 3957–3958.*
Pomp et.al. "Organic Solvents as Facilitators of Poymerase Chain Reaction", Biofeedback, 1991, vol. 10, pp. 58–59.*
Watanabe et.al. "A reproducible assay of PCR to detect trinucleotide repeat . . . " Neurological Research, 1996, vol. 18, pp. 16–18.*
NCBI database Accession # L27350, Feb. 12, 2001, *Homo sapiens* huntingtin (HD) gene, exon 1.*

* cited by examiner

*Primary Examiner*—W. Gary Jones
*Assistant Examiner*—Sally A. Sakelaris
(74) *Attorney, Agent, or Firm*—Rader, Fishman & Grauer PLLC

(57) ABSTRACT

The present invention is a method for synthesis of nucleic acids to amplify an intended nucleic acid in a region in which a GC content is rich, wherein a polyhydric alcohol and/or ammonium sulfate is present in an amplification reaction solution. According to the present invention, it is possible to amplify nucleic acids in a GC rich region efficiently and directly from a sample such as blood containing lots of PCR inhibitory substances without undergoing a process of isolating and purifying the nucleic acid, even though conducting PCR in the GC rich region tends to be difficult using conventional processes even if purified DNA is used.

20 Claims, 2 Drawing Sheets

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Oligonucleotides with a nucleotide sequence of
      the plus strand located within the HLA-A gene region

<400> SEQUENCE: 1
gaaacsgcct ctgygggag aagcaa                                           26

<210> SEQ ID NO 2
<211> LENGTH: 24
<212> TYPE: DNA
<213> ORGANISM: Artificial Sequence
<220> FEATURE:
<223> OTHER INFORMATION: Oligonucleotides with a nucleotide sequence of
      the minus strand located within the HLA-A gene region

<400> SEQUENCE: 2
tgttggtccc aattgtctcc cctc                                            24

METHOD FOR SYNTHESIS OF NUCLEIC ACIDS

BACKGROUND OF THE INVENTION

1. Field of the Invention

The present invention relates to a method for synthesis of nucleic acids, especially to a method for synthesis of nucleic acids by means of a polymerase chain reaction (hereinafter abbreviated as a PCR).

2. Description of the Related Art

A PCR method is a procedure capable of amplifying an intended DNA fragment as much as several hundred thousand-fold by repeating a process comprised of dissociation of a DNA strand into single strands, binding of primers with sandwiching a particular region of the DNA strand, and a DNA synthesis reaction by a DNA polymerase. The PCR method is described in Japanese Laid-open Patent Publication No.S61-274697 which is an invention by Mullis et al.

A PCR procedure can be used as a highly sensitive method for analyzing nucleic acids in various samples. For animals, the PCR procedure is used for searching for genes that cause an infectious disease, a hereditary disease or the like, searching for therapeutics utilizing those genes, diagnosis, monitoring, or the like. The PCR procedure is also suited to DNA typing tests for a transplantation, a paternity test, medical treatments based on an individual genetic information, and the like. For these purposes, a peripheral blood is often selected as a test object. In addition, for plants, the PCR procedure is used for searching for useful genes, monitoring of plants in which these genes are transduced, or the like. For these purposes, a leaf is often selected as a test object.

One drawback of the PCR procedure is that the reaction is inhibited by pigments, proteins, saccharides, or unknown contaminants. Namely, many DNA polymerases including Taq DNA polymerase derived from Thermus aquaticus, a typical thermostable DNA polymerase, are widely known to allow the PCR to be inhibited potently by even a trace amount of living body-derived contaminants existing in the PCR reaction solution.

Therefore, the PCR procedure requires a process in which a cell(s), a fungus (fungi), a bacterium (bacteria), a virus(es) or the like (hereinafter referred to as a nucleic acid inclusion body) are isolated from a subject and then nucleic acids are extracted from the nucleic acid inclusion body prior to a DNA amplification. Such process has conventionally been a procedure in which the nucleic acid inclusion body is decomposed using an enzyme, a surfactant, a chaotropic agent, or the like, and then nucleic acids are extracted from the decomposed product of the nucleic acid inclusion body using, for example, phenol or phenol/chloroform.

Recently, an ion-exchange resin, a glass filter, glass beads, a reagent having an effect of agglutinating proteins, or the like is used in the step of the nucleic acid extraction.

It is difficult, however, to completely remove impurities by purifying nucleic acids in a sample using these procedures, and furthermore, an amount of nucleic acids in a sample recovered by these purification procedures often varies among experiments. For these reasons, a subsequent nucleic acid synthesis may sometimes be unsuccessful, especially when a content of the intended nucleic acid in the sample is low. In addition, these purification procedures involve complicated manipulations and are time-consuming, and there is a high opportunity for contamination during the procedures.

Therefore, a simpler, more convenient and effective method of a sample pretreatment is desired in order to solve these problems.

SUMMARY OF THE INVENTION

The present inventors found that the PCR can be carried out by adding a nucleic acid inclusion body in a sample or the sample itself to a reaction solution for gene amplification, if a pH value of a PCR reaction solution is raised or if polyamines are added to the PCR reaction solution. However, it was found that DNA in the sample sometimes could not be efficiently amplified depending on a region to be amplified, even if above-mentioned method was used. In addition, it is known that the amplification is difficult to be conducted in the case that a content of guanine (G) and cytosine (C) (hereinafter referred to as a GC content) is rich in a region where gene amplification occurs, even if purified DNA is used for the PCR.

Thus, an object of the present invention is to provide a method of treatment that is useful in conducting a nucleic acid synthesis procedure capable of directly amplifying an intended nucleic acid in a living body-derived sample without purification steps.

As a result of eager studies, the present inventors found out that nucleic acids in a region in which a GC content is rich could be amplified if a polyhydric alcohol and/or ammonium sulfate was allowed to be present in a reaction solution, and thus arrived at the present invention.

Namely, the present invention is a method for synthesis of nucleic acids to amplify an intended nucleic acid in a region in which a GC content is rich, wherein a polyhydric alcohol and/or ammonium sulfate is present in an amplification reaction solution. Hereinafter, "a region in which a GC content is rich" is referred to as "a GC rich region".

The present invention is the method for synthesis of nucleic acids wherein a nucleic acid inclusion body in a living body-derived sample or the living body-derived sample itself is added to the amplification reaction solution.

The present invention is the method for synthesis of nucleic acids wherein a pH value of the amplification reaction solution at 25° C. is adjusted to 8.4 or higher and/or that at 70° C. is adjusted to 7.4 or higher.

The present invention is the method for synthesis of nucleic acids wherein the polyhydric alcohol is glycerin.

According to the present invention, it becomes possible to amplify nucleic acids in a GC rich region efficiently in direct manner from a sample such as blood containing lots of PCR inhibitory substances without undergoing a process of isolating and purifying the nucleic acids, although it has been known that the PCR in the GC rich region is difficult to be conducted even if purified DNA is used. It becomes possible by the present invention to conduct synthesis of nucleic acids from a sample more simply, conveniently and rapidly. Further, it becomes also possible to reduce the opportunity for contamination.

DETAILED DESCRIPTION OF THE INVENTION

Figure 1:
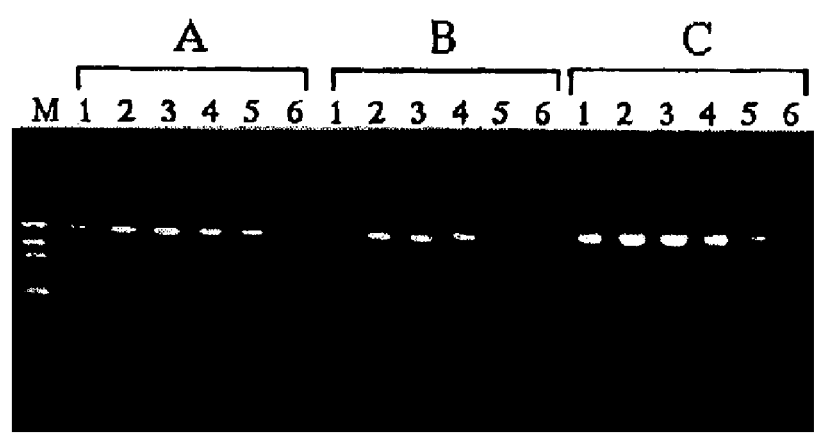
FIG. 1 shows an electrophoretogram of amplified products obtained by the PCR in which human blood treated with an anticoagulant was directly added to PCR reaction solutions in which various concentrations of glycerin were added thereto.

The preset invention is a method for synthesis of nucleic acids to amplify an intended nucleic acid in a region in which a GC content is rich, wherein a polyhydric alcohol and/or ammonium sulfate is present in an amplification reaction solution.

In the present invention, the term "a region in which a GC content is rich" means a region in which a GC content is 40% or more. In particular, considerable effects are obtained in the region in which the GC content is a range from 50% to 70%.

Next, as the polyhydric alcohol, for example, an aromatic polyhydric alcohol such as a compound prepared by addition reaction of ethylene oxide to bisphenol, an aliphatic polyhydric alcohol such as ethylene glycol, propylene glycol, butanediol, hexanediol, octanediol, glycerin, sorbitan, trimethylolpropane and neopentyl glycol, a ether glycol such as diethylene glycol, triethylene glycol, polyethylene glycol and polypropylene glycol, or the like may be used. Among these, the aliphatic polyhydric alcohol is particularly preferred, and further, glycerin and ethylene glycol are preferred.

An amount of the polyhydric alcohol to be used depends on the kind thereof; for example, in the case that glycerin is used as the polyhydric alcohol, the amount of the polyhydric alcohol may be from 2.5% to 20%, preferably from 5% to 15%, with respect to the amplification reaction solution (as used herein, the "%" means a % by volume).

Further, in the present invention, ammonium sulfate may be present in the amplification reaction solution. In the present invention, it is good that ammonium sulfate is present at a concentration in a range from 20 mM to 100 mM, preferably from 40 mM to 80 mM, in the amplification reaction solution. Although ammonium sulfate may be used alone or together with the polyhydric alcohol at the same time, considerable effects are obtained in the case that both of the polyhydric alcohol and ammonium sulfate are used at the same time.

In the present invention, the polyhydric alcohol and/or ammonium sulfate may be added to the sample and then mixed with the amplification reaction solution, or may be added in advance to the amplification reaction solution to be mixing with the sample. Thus, the order of the addition thereof is not specifically limited.

In the present invention, the synthesis of nucleic acids can be conducted by adding a nucleic acid inclusion body in a living body-derived sample or the living body-derived sample itself to the amplification reaction solution. The living body-derived sample includes, but not limited to, various organs, various tissues, various body fluids such as blood (including blood-derived samples such as plasma or serum) and cerebrospinal fluid, various secretions such as milk, saliva and sweat, and various excretions such as feces and urine, in animals. Further, the living body-derived sample includes, but not limited to, roots, stems, leaves, flowers and seeds, in plants.

Here, the term "itself" means that no special pretreatment is required. In the concrete, no following pretreatment is required; the nucleic acid inclusion body is decomposed using an enzyme, a surfactant, a chaotropic agent, or the like, and then nucleic acids are extracted from the decomposed product of the nucleic acid inclusion body using phenol, phenol/chloroform or the like. Further, pretreatment using an ion-exchange resin, a glass filter, glass beads, a reagent having an effect of agglutinating proteins, or the like is not required in the step of the nucleic acid extraction.

In the present invention, a pH value of the amplification reaction solution may be adjusted to 8.4 or higher at 25° C. preferably 8.5 to 8.9 at 25° C. and/or 7.4 or higher at 70° C. preferably 7.5 to 7.9 at 70° C.

Here, in the present invention, a method for nucleic acid amplification comprises a PCR procedure or an RT-PCR procedure, but this method is not limited to these procedures if gene amplification is conducted using an enzyme reaction.

The PCR reaction solution normally contains pH buffer as well as univalent and divalent salts, primers, deoxyribonucleotides and thermostable polymerases. In addition, various substances including proteins such as gelatin and albumin, dimethyl sulfoxide, a surfactant or the like are sometimes added.

The RT reaction solution normally contains a pH buffer as well as univalent and divalent salts, DTT, primers, deoxyribonucleotides, RNase inhibitors and reverse transcriptases. In addition, various substances including proteins such as gelatin and albumin, a surfactant or the like are sometimes added.

The pH buffer is prepared by a combination of tris (hydroxymethyl)aminomethane and a mineral acid such as hydrochloric, nitric, or sulfuric acid, and a preferred mineral acid is hydrochloric acid. Alternatively, various other pH buffers, including pH buffers comprising a combination of Tricine, CAPSO (3-N-cyclohexylamino-2-hydroxypropanesulfonic acid), or CHES (2-(cyclohexylamino)ethanesulfonic acid) and caustic soda or caustic potash, may be used. The pH-adjusted buffer is often used at a concentration within a range from 10 mM to 100 mM in the reaction solution for gene amplification.

The term "a primer" refers to an oligonucleotide that acts as an initiation site of synthesis in cDNA synthesis or nucleic acid amplification. The primer is desirably single-stranded, and a double-stranded primer may also be used. When the primer is double-stranded, it is desirable to convert it into its single-stranded form prior to the amplification reaction. The primers may be synthesized using known methods, or may be isolated from living organisms.

The term "thermostable polymerase" means a polymerase that synthesizes nucleic acids by addis of primers and is superior in heat resistance. A suitable thermostable polymerase includes, but not limited to, Taq DNA polymerase derived from Thermus aquaticus, Thu. DNA polymerase derived from Thermus thermophilus, KOD derived from Pyrococcus, Pfu or Pwo DNA polymerase, a mixture of the aforesaid thermostable DNA polymerases, or the like. Here, since Tth DNA polymerase also has an RT activity, Thu. DNA polymerase has a characteristic capable of conducting RT-PCR in one tube-one step manner by one kind of the enzyme.

The term "a reverse transcriptase" means an enzyme capable of reverse-transcribing RNA to cDNA. The reverse transcriptase includes, but not limited to, a reverse transcriptase derived from a retrovirus of birds such as Rous associated virus (RAV) and Avian myeloblastosis virus (AMV), a reverse transcriptase derived from a retrovirus of mice such as Moloney murine leukemia virus (MMLV), the aforesaid Tth DNA polymerase and others.

The steps constituting a method for synthesis of nucleic acids of the present invention are not different from those steps in the conventional methods with the exception that a reaction solution containing a polyhydric alcohol is used in the case that purified nucleic acids are used, or a solution adjusted to pH 8.4 or higher at 25° C. and/or pH 7.4 or higher at 70° C. containing ammonium sulfate and/or a polyhydric alcohol is used in the case that a nucleic acid inclusion body in a living body-derived sample or the living body-derived sample itself is directly used. Namely, the RT reaction may be conducted at a temperature that is suitable for selected primers and reverse transcriptases for about 30 minutes to 1 hour. In the step of the PCR, following three steps are repeated; an double-stranded DNA is heat-denatured into single-stranded DNAs (a denaturation step); primers by which the region to be amplified is bounded are allowed to hybridize (an annealing step); and DNA polymerase is allowed to act in the presence of four deoxyribonucleotides (dATP, dGTP, dCTP and dTTP) to conduct a primer extension reaction (a polymerization step). Alternatively, the annealing step and the polymerization step may be conducted at the same time.

EXAMPLES

The present invention is further described in the following examples which are not intended to restrict the invention.

Experimental Example 1

To a PCR reaction solution (50.0 µl) was added 1.0 µl of a human blood treated with an anticoagulant (sodium citrate, EDTA-2K or Heparin-Na) to conduct the PCR. The PCR primers were oligonucleotides having a nucleotide sequence of the plus strand (P1, SEQ ID. NO. 1) and the minus strand (P2, SEQ ID. NO. 2) located within the HLA-A gene region, and these sequences were as below. As a result of the PCR using these two primers, 986 bp of an amplified product may be produced. Here, the GC content in this region is 68.6%.

```
P1: 5' GAAACSGCCTCTGYGGGGAGAAGCAA 3'

P2: 5' TGTTGGTCCCAATTGTCTCCCCTC 3'
```

The PCR reaction solution used was a reaction solution comprising 67 mM Tris-HCl adjusted at pH 8.8, 16.6 mM $(NH_4)_2SO_4$, 2.0 mM $MgCl_2$, 200 µM each of dATP, dCTP, dGTP and dTTP, 1.0 µM primers, and 2.5 units/50 µl of Taq DNA polymerase (TaKaRa Z-Taq: Takara Shuzo, Kyoto, Japan) in which 0% to 20% of glycerin was added thereto.

The PCR involved a preheating at 96° C. for 3 minutes, 40 cycles each of which consists 30 seconds at 96° C. followed by 1 minute at 65° C. followed by 1 minute at 72° C., and then the final polymerization at 72° C. for 7 minutes. After the completion of the PCR, 5 µl of the reaction solution was subjected to an electrophoresis on a 2.5% agarose gel in TAE (40 mM Tris-acetate, 1 mM EDTA, pH 8.0) containing 0.5 µg/ml ethidium bromide to detect the amplification products.

FIG. 1 shows the electrophoretogram of amplified products obtained by the PCR in which the human blood treated with the anticoagulant was directly added to the PCR reaction solution. In the figure, lanes A indicate the results obtained with the blood sample treated with sodium citrate; lanes B indicate the results obtained with the blood sample treated with EDTA-2K; lanes C indicate the results obtained with the blood sample treated with Heparin-Na; lanes 1 indicate results obtained with 20% glycerin addition; lanes 2 indicate results obtained with 15% glycerin addition; lanes 3 indicate results obtained with 10% glycerin addition; lanes 4 indicate results obtained with 5% glycerin addition; lanes 5 indicate results obtained with 2.5% glycerin addition; lanes 6 indicate results obtained with 0% glycerin addition.

Also in the figure, a lane M indicates size markers (250 ng of φ X174-RF DNA digested with HincII).

As a result, in the case that the blood sample treated with sodium citrate was used, the PCR amplification products were increased by the addition of glycerin as compared with the results of no glycerin addition. In the case that the blood sample treated with EDTA-2K or Heparin-Na was used, the PCR amplification products were obtained by the addition of glycerin, whereas no PCR amplification product was obtained by no glycerin addition.

Experimental Example 2

This example describes an experiment in which pH values of the PCR reaction solution were adjusted to a range within 8.3 to 8.9 with 10% glycerin addition that afforded best amplification efficiency in the Experimental Example 1 to conduct the PCR. A sample used was the blood sample used in the Experimental Example 1. A composition of the PCR solution, a condition of the PCR and a condition of the electrophoresis after the PCR were the same as in the Experimental Example 1.

Figure 2:
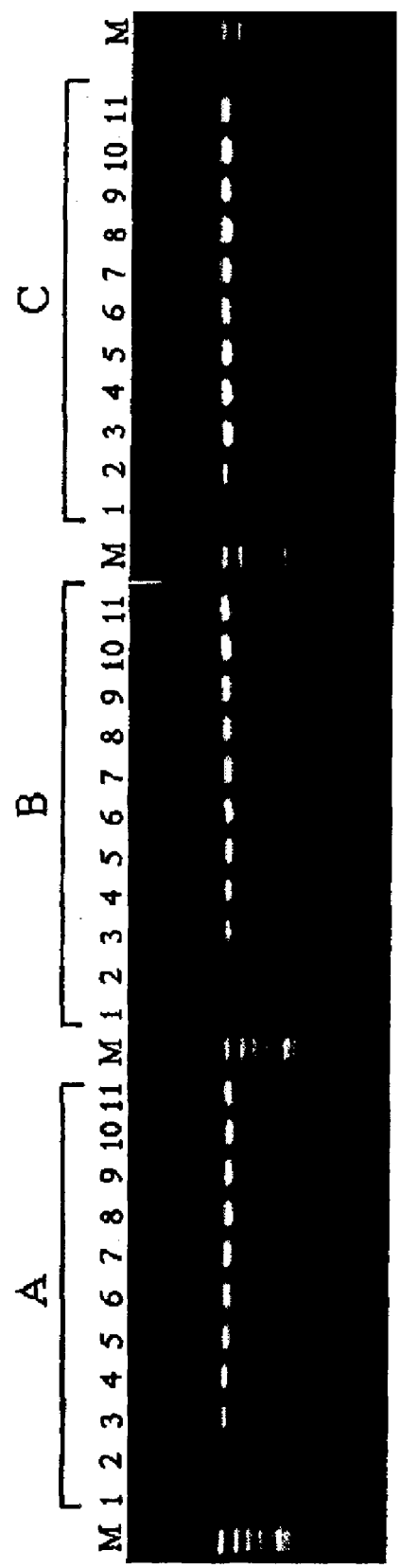
FIG. 2 shows an electrophoretogram of PCR products obtained by the PCR in which human blood treated with an anticoagulant was directly added to PCR reaction solutions that were adjusted to various pH values.

FIG. 2 shows the electrophoretogram of PCR products obtained by the PCR in which the PCR solutions adjusted to various pH values were used to conduct the PCR. In the figure, lanes A indicate the results obtained with the blood sample treated with sodium citrate; lanes B indicate the results obtained with the blood sample treated with EDTA-2K; lanes C indicate the results obtained with the blood sample treated with Heparin-Na; lanes 1 indicate results obtained with the PCR solution adjusted to pH 8.31; lanes 2 indicate results obtained with the PCR solution adjusted to pH 8.39; lanes 3 indicate results obtained with the PCR solution adjusted to pH 8.50; lanes 4 indicate results obtained with the PCR solution adjusted to pH 8.55; lanes 5 indicate results obtained with the PCR solution adjusted to pH 8.61; lanes 6 indicate results obtained with the PCR solution adjusted to pH 8.68; lanes 7 indicate results obtained with the PCR solution adjusted to pH 8.73; lanes 8 indicate results obtained with the PCR solution adjusted to pH 8.80; lanes 9 indicate results obtained with the PCR solution adjusted to pH 8.81; lanes 10 indicate results obtained with the PCR solution adjusted to pH 8.89; lanes 11 indicate results obtained with the PCR solution adjusted to pH 8.80.

As a result, it can be seen that the PCR amplification products were obtained with using the PCR solution adjusted to pH 8.50 or higher, in the case that the blood sample treated with sodium citrate or EDTA-2K was used. It can be seen that the PCR amplification products were obtained with using the PCR solution adjusted to pH 8.39 or higher, in the case that the blood sample treated with Heparin-Na was used.

What is claimed is:

1. A method for synthesis of nucleic acids which comprises: adding a sample comprising a cell, fungus, bacterium, or virus to an amplification reaction solution comprising a polyhydric alcohol and ammonium sulfate, wherein said cell, fungus, bacterium, or virus of said sample is intact and unlysed without extracting and/or purifying said nucleic acid from inside said cell, fungus, bacterium, or virus, when said sample is added to the amplification reaction solution, and directly amplifying said nucleic acid from said intact and unlysed cell, fungus, bacterium, or virus in said amplification reaction solution, said amplification being in a region rich in guanine (G) and cytosine (C) content, wherein said amplifying step consists of (i) preheating said amplification reaction solution, (ii) denaturing said nucleic acid, (iii) annealing a primer to said denatured nucleic acid, and (iv) polymerizing said primer, and wherein said steps(ii), (iii), and (iv) of said amplifiying step are repeated.

2. The method for synthesis of nucleic acids according to claim 1, wherein said amplifying step comprises at least one of adjusting a pH value of the amplification reaction solution to 8.4 or higher if the reaction solution is about 25° C., and adjusting a pH value of the amplification reaction solution to 7.4 or higher if the reaction solution is about 70° C.

3. The method for synthesis of nucleic acids according to claim 1, wherein the GC content in the GC rich region is 40% or more.

4. The method for synthesis of nucleic acids according to claim 1, wherein the GC content in the GC rich region is a range from 50% to 70%.

5. The method for synthesis of nucleic acids according to claim 1, wherein the polyhydric alcohol is selected from the group consisting of an aromatic polyhydric alcohol, an aliphatic polyhydric alcohol and an ether glycol.

6. The method for synthesis of nucleic acids according to claim 5, wherein the aliphatic polyhydric alcohol is selected from the group consisting of ethylene glycol, propylene glycol, butanediol, hexanediol, octanediol, glycerin, sorbitan, trimethylolpropane and neopentyl glycol.

7. The method for synthesis of nucleic acids according to claim 6, wherein the aliphatic polyhydric alcohol is glycerin.

8. The method for synthesis of nucleic acids according to claim 7, wherein glycerin is contained in a range from 2.5% to 20% by volume in the amplification reaction solution.

9. The method for synthesis of nucleic acids according to claim 6, wherein the aliphatic polyhydric alcohol is ethylene glycol.

10. The method for synthesis of nucleic acids according to claim 1, wherein ammonium sulfate is present at a concentration from 20 mM to 100 mM in the amplification reaction solution.

11. A method for synthesis of nucleic acids, which comprises:

adding a cell fungus, bacterium, or virus to an amplification reaction solution comprising a polyhydric alcohol and ammonium sulfate, wherein said cell, fungus, bacterium, or virus is added to the amplification reaction solution intact and unlysed without extracting and/or purifying said nucleic acid from inside said cell, fungus, bacterium, or virus, and directly amplifying said nucleic acid from said intact and unlysed cell, fungus, bacterium, or virus in said amplification reaction solution, said amplification being in a region rich in guanine (G) and cytosine (C) content, wherein said amplifying step consists of (i) preheating said amplification reaction solution; (ii) denaturing said nucleic acid, (iii) annealing a primer to said denatured nucleic acid, and (iv) polymerizing said primer, and wherein said steps (ii), (iii), and (iv) of said amplifiying step are repeated.

12. The method for synthesis of nucleic acids according to claim 11, wherein said amplifying step comprises at least one of adjusting a pH value of the amplification reaction solution to 8.4 or higher if the reaction solution is about 25° C., and adjusting a pH value of the amplification reaction solution to 7.4 or higher if the reaction solution is about 70° C.

13. The method for synthesis of nucleic acids according to claim 11, wherein the GC content in the GC rich region is 40% or more.

14. The method for synthesis of nucleic acids according to claim 11, wherein the GC content in the GC rich region is a range from 50% to 70%.

15. The method for synthesis of nucleic acids according to claim 11, wherein the polyhydric alcohol is selected from the group consisting of an aromatic polyhydric alcohol, an aliphatic polyhydric alcohol and an ether glycol.

16. The method for synthesis of nucleic acids according to claim 15, wherein the aliphatic polyhydric alcohol is selected from the group consisting of ethylene glycol, propylene glycol, butanediol, hexanediol, octanediol, glycerin, sorbitan, trimethylolpropane and neopentyl glycol.

17. The method for synthesis of nucleic acids according to claim 16, wherein the aliphatic polyhydric alcohol is glycerin.

18. The method for synthesis of nucleic acids according to claim 17, wherein glycerin is contained in a range from 2.5% to 20% by volume in the amplification reaction solution.

19. The method for synthesis of nucleic acids according to claim 16, wherein the aliphatic polyhydric alcohol is ethylene glycol.

20. The method for synthesis of nucleic acids according to claim 11, wherein ammonium sulfate is present at a concentration from 20 mM to 100 mM in the amplification reaction solution.

* * * * *